(12) United States Patent
Clark

(10) Patent No.: US 6,719,896 B1
(45) Date of Patent: Apr. 13, 2004

(54) FLUID-FILTRATION RECEPTACLE WITH USER-VARIABLE SEMI-PERMEABLE DRAIN ASSEMBLY

(75) Inventor: Phillip Clark, Wakefield, MA (US)

(73) Assignee: Millipore Corporation, Billerica, MA (US)

( * ) Notice: Subject to any disclaimer, the term of this patent is extended or adjusted under 35 U.S.C. 154(b) by 155 days.

(21) Appl. No.: 10/056,301

(22) Filed: Jan. 23, 2002

(51) Int. Cl.7 .................... B01D 35/14; B01D 17/12
(52) U.S. Cl. ................. 210/91; 210/247; 210/248; 210/360.1; 210/321.84; 494/16; 494/36
(58) Field of Search ................ 210/247, 321.68, 210/321.84, 360.1, 380.1, 514, 515, 518, 650, 781, 473, 474, 91, 163; 494/16, 20, 36; 422/61, 72, 101; 436/177, 178

(56) References Cited

U.S. PATENT DOCUMENTS

| | | | |
|---|---|---|---|
| 4,632,761 A | | 12/1986 | Bowers et al. ............... 210/650 |
| 4,722,792 A | | 2/1988 | Miyagi et al. ............ 210/360.1 |
| 5,032,264 A | * | 7/1991 | Geiger ......................... 210/163 |
| 5,227,062 A | * | 7/1993 | Olsen ......................... 210/321.6 |
| 5,308,483 A | * | 5/1994 | Sklar et al. .................. 210/232 |
| 5,647,990 A | | 7/1997 | Vassarotti ..................... 210/650 |
| 5,948,246 A | * | 9/1999 | Zuk, Jr. ...................... 210/188 |
| 6,344,140 B1 | * | 2/2002 | Zuk, Jr. ................... 210/321.84 |
| 6,537,446 B1 | * | 3/2003 | Sanguinetti ................. 210/163 |

* cited by examiner

Primary Examiner—Joseph Drodge
(74) Attorney, Agent, or Firm—Renato M. de Luna

(57) ABSTRACT

The present invention provides a fluid-filtration receptacle well-suited for use in centrifugal sample concentration protocols, and particularly, wherein specifiable degrees of sample concentration are sought. Toward this end, the fluid-filtration receptacle is provided with an integral semi-permeable drain capable of being either completely or variably unsealed by a user to allow selective draining of a predetermined corresponding volume of said liquid from said receptacle. The fluid-filtration receptacle is preferably used in combination with a filtrate collection vial. The receptacle fits at least partially within the vial such that liquid (i.e., filtrate) drained from said receptacle collects within said vial.

12 Claims, 8 Drawing Sheets

FLUID-FILTRATION RECEPTACLE WITH USER-VARIABLE SEMI-PERMEABLE DRAIN ASSEMBLY

FIELD

The present invention relates in general to a fluid-filtration receptacle, and more particularly, to a fluid-filtration receptacle (such as used in a centrifugal filter unit) provided with a user-variable semi-permeable drain assembly.

BACKGROUND

Biomolecules—such as proteins and nucleic acids—continue to be the subject of intense and broad academic and commercial investigation. Investigation, of course, requires detection. While detection instruments and methodologies continue to evolve in their sophistication, precision, and sensitivity, sample preparation remains important, if not more so. Often, sample contain only minute or trace amounts of a biomolecule being investigated, and accordingly, sample concentration is frequently desired to assure and/or facilitate its detection. Certain detection methodologies also perform better within certain sample volume ranges.

A variety of centrifugal filter units are currently available and continue to be used with good results for sample preparation. Centrifugal filter units commonly comprise a housing to hold the unfiltered sample, a collection tube for the filtered sample, a filter sealed in a manner so that when the sample passes from the housing to the collection tube it must pass through the filter, and a means to collect the concentrated sample from the housing.

Centrifugal filter units are commonly spun in centrifuges using either of two basic types of rotors: i.e., "swinging bucket" and "fixed angle". The fixed angle rotor positions the device at a preset angle relative to the axis of rotation or g-force. In the swinging bucket rotor, the device swings out into a position such that the device is or almost parallel to the axis of rotation or g-force. In centrifuges, the maximum forces are generated at the outermost point along the radius of rotation.

To concentrate a component in a liquid sample with a centrifuge device, two features must be present. The membrane or filter must retain the component of interest. This is achieved by having the pores of the membrane smaller than the component so that the component physically can not pass through the membrane. Also, there must be a pocket that is positioned at the outermost point within the housing along the axis of rotation. The pocket must also be positioned relative to the membrane so that liquid in the pocket is not available to flow through the membrane.

In U.S. Pat. No. 4,632,761, issued to W. F. Bowers et al. on Dec. 30, 1986, a device for use in a fixed angle centrifuge rotor is disclosed. The method suggested by Bowers et al. to create a pocket for the concentrate is to either seal the device off or block the downstream side of the membrane by the underdrain structure. The membrane in this device is perpendicular to the centerline of the device. When this device is positioned and spun in a fixed angle centrifuge rotor, the g-force acts at an angle relative to the membrane surface. As the liquid filters through the membrane, a small amount of liquid stops flowing because the g-force pushes the liquid into the pocket. The device side walls of the housing and the outlet holes of the underdrain support structure define this pocket. The volume will change slightly by spinning the device in a rotor with a different fixed angle. Changing the rotor may result is in a more useful concentrate volume, but changing rotors is not a practical approach due to the time and skill required to do so.

In U.S. Pat. No. 4,722,792, issued to T. Miyagi et al. on Feb. 2, 1988, and U.S. Pat. No. 5,647,990, issued to V. Vassarotti on Jul. 15, 1997, there are described centrifuge receptacles wherein a membrane is positioned along one or more of the receptacles' sidewalls. The membranes are sealed and supported by an underdrain support. When centrifuged, the filtering stops at the membrane seal. More particularly, filtering stops at the highest point in the seal positioned furthest along the axis of rotation. The concentrate volume is preset by the geometry of the pocket formed in the device, and is not intrinsically variable.

The cited patents are representative of the general design of currently-available centrifuge receptacles, i.e., wherein the maximum filtration volume is fixed either by the structure and geometry of the receptacle's physical configuration and/or the positioning of its installed membrane. Accordingly, to attempt filtration of a volume less than the maximum preset value, the current practice—commonly requiring skilled user intervention during filtration—is to attempt to stop the filtration process at a time that yields the desired volume. This process can be inconsistent and inaccurate, relies heavily on the experience and skill of the user, and can vary depending on sample viscosity, clogging factors in the sample, membrane characteristics, the starting volume of the sample, and other factors.

When working with a fixed angle centrifuge, two options are available to control the filtration volume. The centrifuging process could be stopped at a time that yields the desired volume. As mentioned, this is unreliable. Alternatively, one could obtain and select among a range of different interchangeable rotors having varying rotor angle. The angle will effect concentration volume, but changing centrifuge rotors—though possible—is not a simple matter. It requires time and skill, and thus, may be impractical.

In light of the above, there is a need for a better means for filtering a sample liquid to a variable user-specifiable volume, and particularly, a means that does not require inordinate human intervention and/or oversight once a filtration process on the sample has commenced.

SUMMARY

In response to the above needs, the present invention provides a fluid-filtration receptacle capable of filtration, out of the confines of said receptacle, of specifiable volumes of a sample liquid within a predefined volume range. Toward this end, the fluid-filtration receptacle is provided with and characterized by a semi-permeable drain assembly.

More particularly, in respect of its basic structure, the fluid-filtration receptacle comprises a user-fillable liquid-containable internal area, the boundaries of which are defined by an at least partially-enclosing liquid-impermeable solid material (cf., the receptacle walls). The liquid-impermeable solid material having a releasably-sealed semi-permeable drain assembly disposed therethrough. Although subject to variation, in all instances, the semi-permeable drain assembly will be capable of being either completely or variably unsealed by a user to allow draining of a predetermined corresponding volume of a sample liquid from said internal area when the fluid-filtration receptacle is placed in at least one of said predetermined operative positions.

As will be appreciated by those skilled in the art, the fluid-filtration receptacle can find utility in several and various analytical separation methods, and accordingly, will be therein embodied to conform, within the definition of the present invention, with the structural and functional requirements associated therewith. One important method is centrifugation.

In centrifugation, the fluid filtration receptacle will typically be used in combination with a filtrate collection vial, the combination being placed together in a centrifuge holder during a centrifugal operation. Several of the embodiments of the present invention are drawn to applicability within the several classes of centrifuges currently available, the two basic division thereof being so-called "swinging bucket rotor" centrifuges and so-called "fixed angle rotor" centrifuges. Hence, embodiments are provided herein wherein the semi-permeable drain assembly comprises, for example, several sealed openings each capable of being individually and completely unsealed by a user; or a single sealed semi-permeable opening capable of being variably unsealed by a user; or several discrete openings each comprising a releasable seal and a semi-permeable membrane. Other variations involve the configuration and placement of the drain assembly, the configuration and composition of the seal, and the size and shape of the receptacle.

In light of the above, it is a principal object of the present invention to provide a fluid-filtration receptacle capable of filtering specifiable volumes of a sample liquid.

It is another object of the present invention to provide a fluid-filtration receptacle having integrated therein a releasably-sealed semi-permeable drain assembly that is capable of being either completely or partially unsealed by a user to allow either filtered or selective drainage of a specifiable corresponding volume of the sample liquid.

It is another object of the present invention to provide a fluid-filtration receptacle having integrated therein a releasably-sealed semi-permeable drain assembly, the fluid-filtration receptacle being comparatively easy to manufacture and comparatively easy to use.

It is another object of the present invention to provide a centrifugal filter unit capable of concentrating a sample liquid by removing by filtration in a centrifuge specific volumes of liquid from said sample, the concentration being accomplished without critical reliance on the duration of the centrifugal operation.

It is another object of the present invention to provide a centrifugal filter unit comprising (pre-assembled or in a kit) a fluid filtration receptacle and a filtrate collection vial, the fluid-filtration receptacle being (or capable of being) snugly "nested" in the filtrate collection vial.

For further understanding of the nature and objects of the invention, reference should be had to the detailed description further below considered in conjunction with the accompanying drawings.

BRIEF DESCRIPTION OF THE DRAWINGS

Each of FIGS. 1 to 11 provide schematic representational illustrations. The relative location, shapes, and sizes of objects have been exaggerated to facilitate discussion and presentation herein.

DETAILED DESCRIPTION

Figure 1:
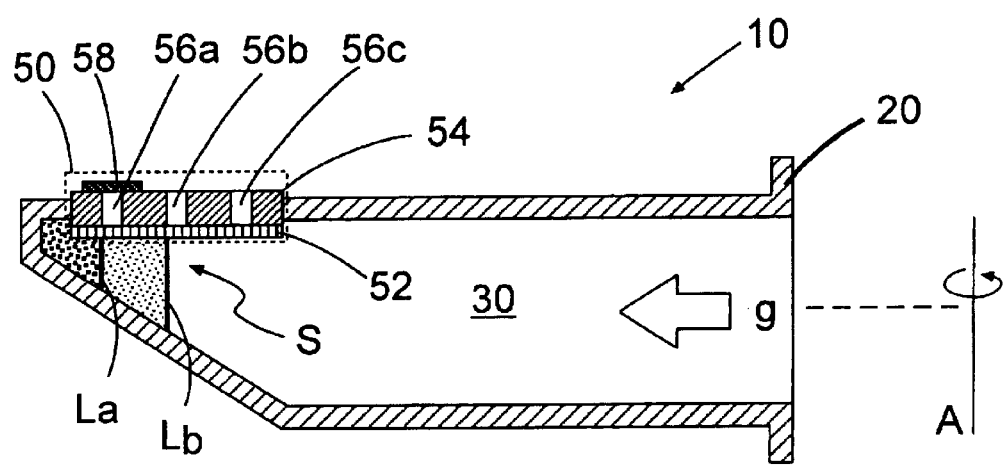
FIG. 1 is a lateral sectional view of a centrifugal fluid-filtration receptacle 10 according to an embodiment of the present invention, the receptacle 10 being particularly adapted for use in a so-called "swinging bucket rotor" centrifuge.

The present invention provides a fluid filtration a fluid-filtration receptacle capable of containing a liquid when placed in a predetermined range of operative positions prior to use in a filtration process and configured to filter a user-specifiable volume of said liquid in the course of said filtration process without user intervention. The receptacle comprises a user-fillable liquid-containable internal area defined by an at least partially-enclosing liquid-impermeable solid material (cf., the receptacle wall). Most importantly, the liquid-impermeable solid material has a releasably-sealed semi-permeable drain disposed therethrough, the semi-permeable drain capable of being either completely or variably unsealed by a user to allow draining of a predetermined corresponding volume of said liquid from said internal area when said receptacle is placed in at least one of said predetermined range of operative positions.

The liquid-impermeable solid material, which essentially forms the major wall surfaces of the receptacle, can be prepared from various materials in varying shapes having varying physical dimensions, the only critical limitation being that the resultant receptacle configuration be capable of containing a liquid when placed in a predetermined range of operative positions. Or very simply stated: It must hold water when upright.

For receptacles intended for use in a centrifugal filter unit, the term "upright" as used herein does not necessarily imply that the receptacle does or can stand (with or without support) substantially orthogonally straight. In fact, the operative "upright" positions of receptacles used for centrifugation are commonly angled correspondent with the inclination angle at which centrifugal filter units are spun within the centrifuge. Typically, in so-called "swinging bucket" and "fixed angle" centrifuges the angles of inclination (relative to the plane of rotation) are about 5 and 45 degrees, respectively.

Useful materials for the receptacle walls can be organic, inorganic, or combinations thereof, and can be natural or synthetic. Typical inorganic materials include glass and ceramics. Organic materials—which are preferred in respect of costs and suitability for mass production—typically include thermocurable and thermoformable polymers and resins. Typical polymers and resins include, but are not limited to, phenolaldehyde resins, melamine-aldehyde resins, thermosetting artificial rubbers, acrylic resins, urethane resins, silicone resins, polysulfides, acetals, cellulosics, fluorocarbons, vinyls, styrenes, and polyethylene, polypropylene, and other polymerized olefinically-unsaturated monomers, and the like. In respect of receptacles for use in biochemical centrifugal operations, particularly where low protein binding is desired, the preferred materials include polycarbonate, polyethylene, and polypropylene.

The semi-permeable drain used in the inventive receptacle provides the means by which a user can select the extent to which sample liquid is filtered out of the receptacle, for example, in the course of centrifugation. This functionality is accomplished essentially by the cooperative interplay of three basic sub-components: i.e., the semi-permeable drain's seal(s), drain hole(s), and membrane(s). Its seal(s) effect selectivity. Its drain hole(s) effect drainage. And, its membrane(s) effect permeability.

In a general configuration, the membrane component is substantially coextensive with the drain hole component such that any liquid flowing through the drain hole component will also flow through the membrane component. The seal component is positioned relative to the drain hole component to prevent the flow of said liquid therethrough. Thus, but for the seal, liquid would otherwise be flowable through the drain hole component. According to the present invention, the seal component is capable of being either partially or completely removed, hence enabling a user to regulate the extent to which liquid is able to flow out of the receptacle.

Provided that the semi-permeable drain is appropriately located on the receptacle relative to its intended operable "upright" position, and provided with an appropriate drain hole/seal configuration, a user is able to select easily the final retentate volume left in the receptacle after its use by variably releasing the seal configuration. This functionality can be enhanced by providing informative indicia on the receptacle in close proximity to a seal indicative of the retentate volume retained or filtrate volume drained resulting from the removal thereof.

The seal and drain hole components are subject to variation in respect of their number, their structure and geometry, and their material manufacture. Certain of these varying embodiments are illustrated in the attached Figures and described in greater detail hereinbelow. See e.g., semi-permeable drain assemblies 50, 250, 450, 550, and 650 in the Figures.

In general, however, in respect of their numbers, the drain hole and seal components can each comprise a single element or a plurality of elements, e.g., a plurality of drain holes with a corresponding plurality of independently removable seals; or a plurality of drain holes aligned along measured distances with a plurality of superposed independent removable seals; or a plurality of drain holes aligned along measured distances with a single variably removable seal superposed thereon; or a single drain hole covered with a variably removable seal; or a single drain hole covered with a plurality of independently removable seals.

In respect of their structure and geometry, several shapes and relative geometric arrangements are available, e.g., the drain hole(s) can form a spiral arrangement of evenly spaced circular holes, or a single elongate slot running the bottom dorsal length of the receptacle, or a plurality of linearly-arranged evenly-spaced openings; and the seals can be formed as removable tabs, or tear away strips, or a puncturable foil covering, or a strippable elastomeric coating.

In respect of their material manufacture, the drain hole and seal components can each be integral to the receptacle wall (i.e., formed of and continuous with the receptacle wall material) or can be assembled thereonto, e.g., drain holes formed by piercing or punching or otherwise providing an opening directly into the receptacle wall, or a drain hole formed through a base plate installed into and through the receptacle wall, or tabular seals formed contemporaneously with the injection molding of a receptacle, or a foil wrapper overlaid onto the drain hole component subsequent to the formation thereof.

Materials useful for the manufacture of the membrane filter include synthetic or natural compositions and may be inorganic, organic, or mixtures thereof. Typical inorganic materials include, but are not limited to, glasses, ceramics, metals, cermets (i.e., ceramic/metal composites), and the like. The organic materials are generally polymeric in nature, and can be substituted or unsubstituted. Typical polymers include, but are not limited to, polysulfones; polystyrenes, including styrene-containing copolymers such as acrylonitrile-styrene copolymers, styrene-butadiene copolymers and styrene-vinylbenzylhalide copolymers; polycarbonates; cellulosic polymers, such as cellulose acetate-butyrate; cellulose propionate, ethyl cellulose, methyl cellulose, nitrocellulose, etc.; polyamides and polyimides, including aryl polyamides and aryl polyimides; polyethers; poly(arylene oxides) such as poly(phenylene oxide) and poly(xylylene oxide); poly(esteramide-diisocyanate); polyurethanes; polyesters (including polyarylates) such as poly(ethylene terephthalate), poly (alkyl methacrylates), poly(alkyl acrylates), poly(phenylene terephthalate), etc.; polysulfides; poly(siloxanes); polymers from monomers having the alpha-olefinic unsaturation other than mentioned above such as poly(ethylene), poly (propylene), poly(butene-1), poly(4-methyl pentene-1), polyvinyls, e.g., poly(vinyl chloride), poly(vinyl fluoride), poly(vinylidene chloride), poly(vinylidene fluoride), poly (vinyl alcohol), poly(vinyl esters) such as poly(vinyl acetate) and poly(vinyl propionate), poly(vinyl pyridines), poly(vinyl pyrrolidones), poly(vinyl ethers), poly(vinyl ketones), poly(vinyl aldehydes) such as poly(vinyl formal) and poly(vinyl butyral), poly(vinyl amides), poly(vinyl amines), poly(vinyl phosphates), and poly(vinyl sulfates); polyallyls; poly(benzobenzimidazole); polyhydrazides; polyoxadiazoles; polytriazoles; poly(benzimidazole); poly-carbodiimides; polyphosphazines; etc., and interpolymers, including block interpolymers containing repeating units from the above and grafts and blends containing any of the foregoing. Typical substituents include halogens; such as fluorine, chlorine and bromine; hydroxy groups; lower alkyl groups; lower alkoxy groups; monocyclic aryl; lower acyl groups; and the like.

Regenerated cellulose ultrafiltration membranes (e.g., "Ultracel Amicon YM" and "Ultracell PL" membranes available from Millipore Corporation of Bedford, Mass.) are well-suited for receptacles targeted for concentrating or desalting extremely dilute or hydrophobic sample liquids. The use of a hydrophilic membrane having a "tight" microstructure promotes good retention with low adsorption of protein, DNA, and other macromolecules. Polyethersulfone ultrafiltration membranes (e.g., "Amicon PM" and "Biomax PB" also available from Millipore Corporation), or other like membrane having an "open" microstructure suitable for rapid separation, are better-suited for receptacles targeted for concentrating and desalting more concentrated sample liquids, such as serum, plasma, and conditioned tissue culture.

Methods for the manufacture of membranes are well documented, for example, in the patent literature. See e.g., U.S. Pat. No. 5,217,802, issued to L. Scarmoutzos on Jun. 8, 1993; U.S. Pat. Nos. 5,037,457; 4,954,256, issued to P. Degen on Sep. 4, 1990; U.S. Pat. No. 5,037,457, issued to P. Goldsmith et al. on Aug. 6, 1991; and U.S. Pat. No. 5,554,414, issued to W. Moya et al. on Sep. 10, 1996.

In a typical centrifugal operation, the receptacle of the present invention is employed within a centrifugal filter unit in combination with a filtrate collection vial. Although the receptacle and vial will have to be assembled ultimately into a finished centrifugal filter unit prior to centrifugation, the constituent parts of the centrifugal filter unit can be provided to an end-user in packaged kit form, with instructions for the assemblage thereof. The packaged kit can include components needed for the assembly of a single or several centrifugal filter units. Preferably, the packaging is hermetic and its contents sterile.

Figure 11:
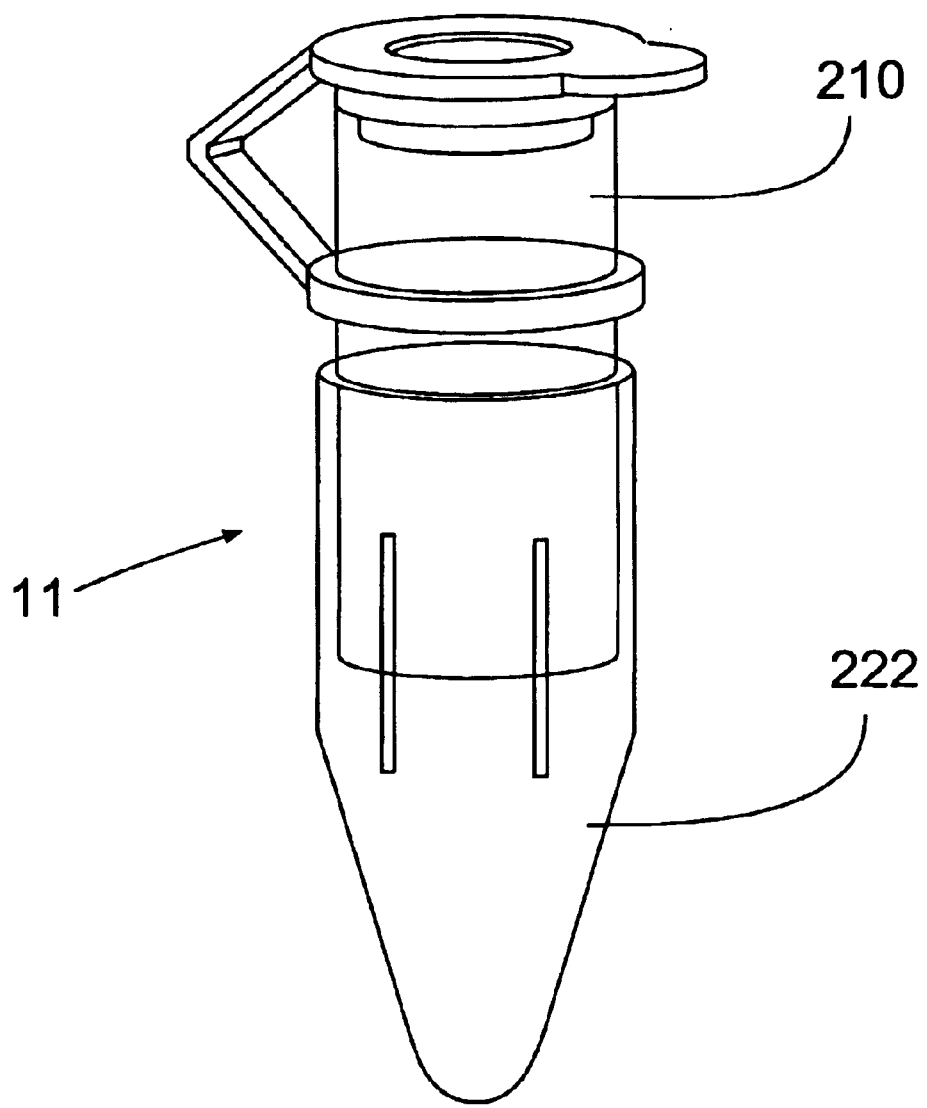
FIG. 11 illustrates a centrifugal filter unit comprising the centrifugal fluid-filtration receptacle 210 shown in FIG. 2 nested within filtrate collection vial 222.

An example of a single centrifugal filter unit is illustrated in FIG. 11. As shown therein, a centrifugal filter unit 11 comprises an inventive receptacle 210 (i.e., a receptacle provided with a releasably-sealed semi-permeable drain) and a filtrate collection vial 222. The receptacle 210 is nested within filtrate collection vial 222 such that sample liquid—loaded into the receptacle 210 and subjected to appropriate pressures and/or other forces (for example, as generated in the course of centrifugation)—can be filtered out of the receptacles drain (not shown in FIG. 11, but see FIG. 2) without physical hindrance, blockage, or occlusion, and be reliably collected within vial 222. The respective load volumes of the vial and receptacle should be established to avoid overflow and spillage in such situation, as well as assure that filtration can be brought to the desired level of completion before the volume available in the collection vial is consumed.

Although the filtrate collection vial in FIG. 11 is shown with an integral cap capable of sealing the opening of receptacle 210, when said receptacle 210 is nested within vial 222, the use of such cap is not in all instances required, nor is it required that, if a cap is used, said cap should be integral with said vial 222. Regardless, if a cap or other covering is used, measures should be taken to avoid formation of an internal vacuum within the combined filter unit that may substantially preclude or otherwise reduce the efficacy of filtration through the semi-permeable drain.

The structural configuration of a filtrate collection vial is subject to much variation, and will to large extent depend on the structural configuration of the sample receptacle. Representative examples of centrifugal filter units are disclosed, for example, in U.S. Pat. No. 4,722,792, issued to T. Miyagi et al. on Feb. 2, 1988; U.S. Pat. No. 5,647,990, issued to V. Vassarotti on Jul. 15, 1997; and U.S. Pat. No. 4,632,761, issued to W. F. Bowers et al. on Dec. 30, 1986.

The filtrate collection vial, like the receptacle, are preferably injection molded thermoplastic material, and are of such low cost that the centrifugal filter unit can be disposed after a single-use.

It should be apparent that the present invention described herein invites and accommodates several and broad variation in respect, for example, of its structure, manufacture, and application. Provided with the teachings herein, the practice of all such particular embodiments are felt to fall within the "skill in the art". Regardless, representative (non-limiting) examples of such inventive embodiments, and varying components and applications thereof, are set forth in FIGS. 1 to 11.

Referring to FIG. 1, a fluid-filtration receptacle 10 is shown, as it would be in a swinging bucket rotor. The centrifugal force (g-force) acts along the radius about the axis of rotation A. When the fluid-filtration receptacle 10 is spun in a centrifuge (not shown), the sample liquid S is forced to the outermost part of the fluid-filtration receptacle 10 about the axis of rotation A. The housing 20 is shown with a membrane 52 sealed to an underdrain support 54. The underdrain support 54 has a set of drain holes 56a, 56b, and 56c. The underdrain support 54 is sealed liquid tight to the housing 20. When the receptacle 10 is spun in a centrifuge the liquid in the housing 20 will pass through the membrane 52 and out the drain holes 56a, 56b, and 56c in the underdrain support 54. A sealing device 58 is shown covering the outermost drain hole 56a. When centrifuged, the sample liquid in receptacle 10 will pass through the membrane 52 and out of drain holes 56b and 56c. The filtration will stop at the point where the sample liquid can no longer exit drain hole 56b leaving a concentrate volume shown as level $L_b$. If the sealing device 58 were to be removed from all drain holes 56a, 56b, and 56c prior to centrifugation, the filtering process would stop at level $L_a$.

Figure 2:
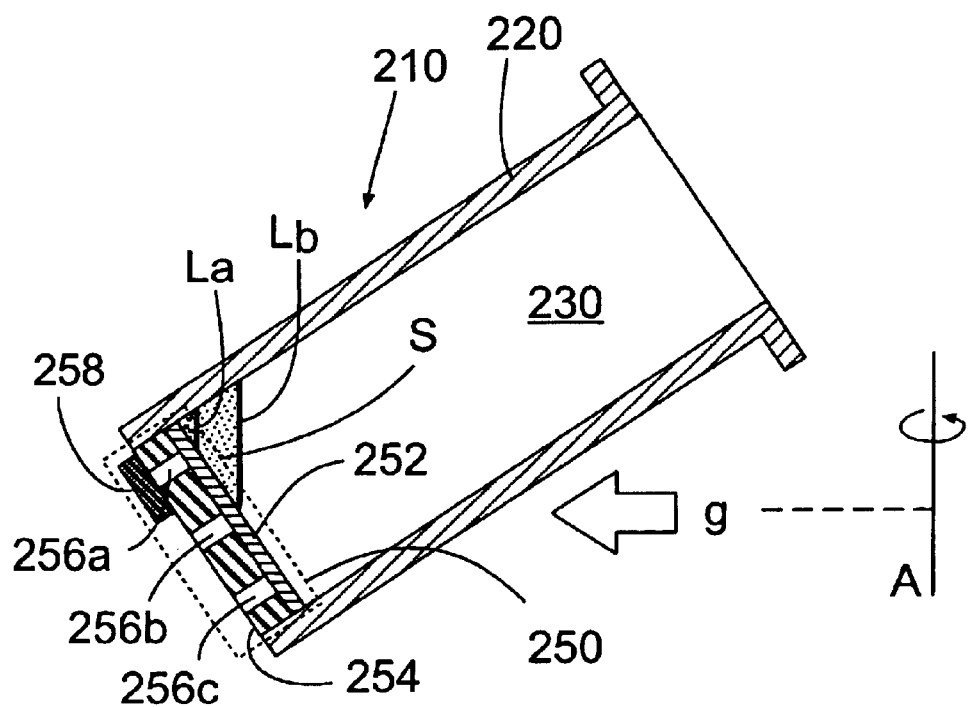
FIG. 2 is a lateral sectional view of a centrifugal fluid-filtration receptacle 210 according to another embodiment of the present invention, the receptacle being particularly adapted for use in a so-called "fixed angle rotor" centrifuge.

Referring to FIG. 2, a fluid-filtration receptacle 210—having a configuration suitable for use in a fixed-angle rotor centrifuge—is shown, as it would be in a fixed angled rotor. The centrifugal force g acts along the radius about the axis of rotation A. When the fluid-filtration receptacle 210 is spun in a centrifuge the sample S is forced to the outermost part of the device 210 about the axis of rotation A. The housing 220 is shown with a membrane 252 sealed liquid tight to the perimeter of an underdrain support 254. The underdrain support 254 has a set of drain holes 256a, 256b, and 256c. The underdrain support 254 is sealed liquid tight to the housing 220. When the receptacle 210 is spun in a fixed angled centrifuge, the sample S in the housing 220 will pass through the membrane 252 and out the drain holes 256a, 256b, and 256c in the underdrain support 254. A sealing device 258 is shown covering the outermost drain hole 256a. When centrifuged the sample S in receptacle 210 will pass through the membrane 252 and out of drain holes 256b and 256c. The filtration will stop at the point when the filtered solution can no longer exit drain hole 256b leaving a concentrate volume shown as level $L_b$. If the sealing device 258 were to be removed from drain hole 256a prior to centrifugation the filtering process would stop at level $L_a$.

The principles of operation are the same for other like receptacles, whether designed for use in a swinging bucket or a fixed angled centrifuge. The liquid moves to the outermost point about the axis of rotation and exits the outermost drain that is open to flow.

Figure 3:
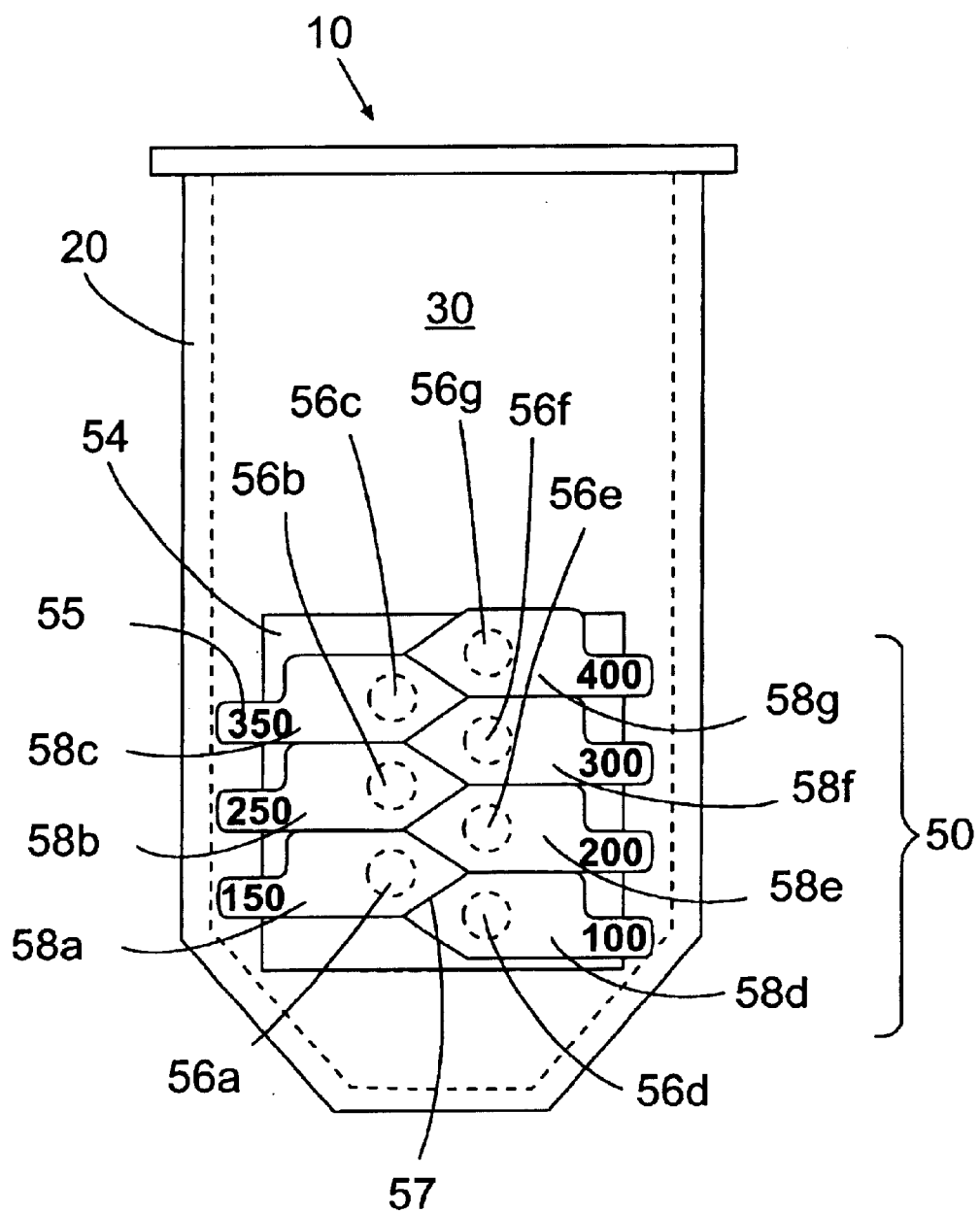
FIG. 3 is a frontal view of the centrifugal fluid-filtration receptacle 10 illustrated in FIG. 1.

FIG. 3 shows the front of the fluid-filtration receptacle 10 illustrated in FIG. 1. The fluid-filtration receptacle 10 is provided with an underdrain support 54 sealed liquid tight into housing 20. A set of drain holes 56a–g are covered and sealed by a corresponding set of sealing devices 58a–g. Selection of the desired final concentration volume prior to centrifugation is made by peeling off the appropriate sealing device. Preferably, all of the sealing device(s) above the desired concentration level are removed to ensure a rapid filtration by exposing as many available drain holes for the volume desired. In the present embodiment, the sealing devices 58a–g are labeled with preset volumes from 100–400 volume units. By removing sealing device 58e and then processing the sample, the final concentrate volume in the receptacle 10 will be 300 volume units. Once the preset concentrated volume has been reached, the device will stop filtering even if the device is spun for additional time. The sealing devices 58a–g can be precut and separated by a small cut 57 between each sealing device 58a–g. The material of sealing device 58a–g can be an adhesive backed film.

Figure 4:
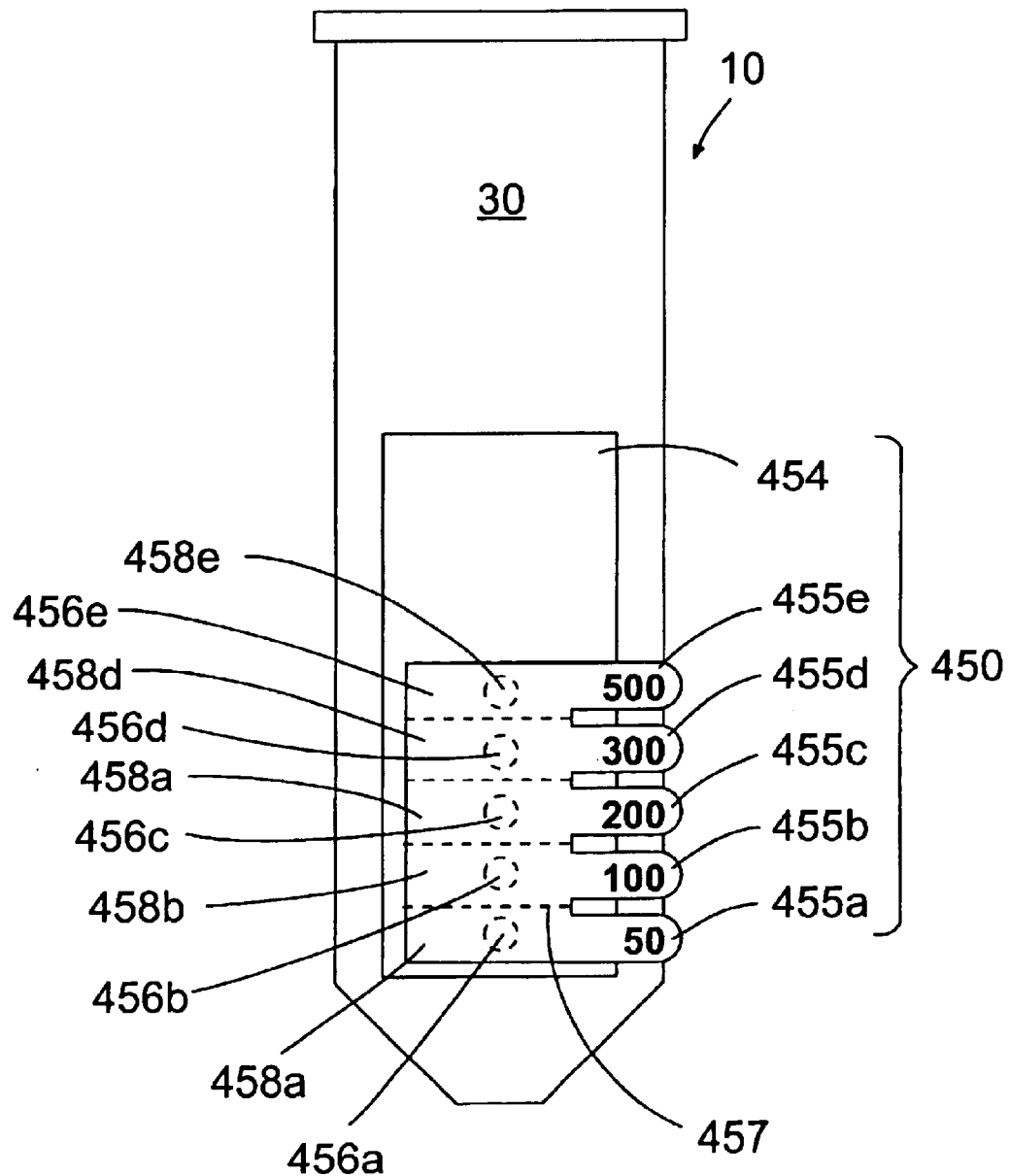
FIG. 4 is a frontal view of a fluid-filtration receptacle 10 according to another embodiment of the present invention, the embodiment being distinguished primarily by the configuration of the receptacle 10's releasably-sealed semi-permeable drain 450.

In another embodiment, shown in FIG. 4, the sealing device 458a–e covering drain holes 456a–e is a solid film with perforations 457 between adjacent sealing elements (e.g., elements 458a and 458b). The perforations 457 separate each of the sealing devices 458a–e. The sealing device can be removed by pulling the tab 455a–e corresponding to the desired concentrate volume, exposing the corresponding drain hole 456a–e.

Figure 5:
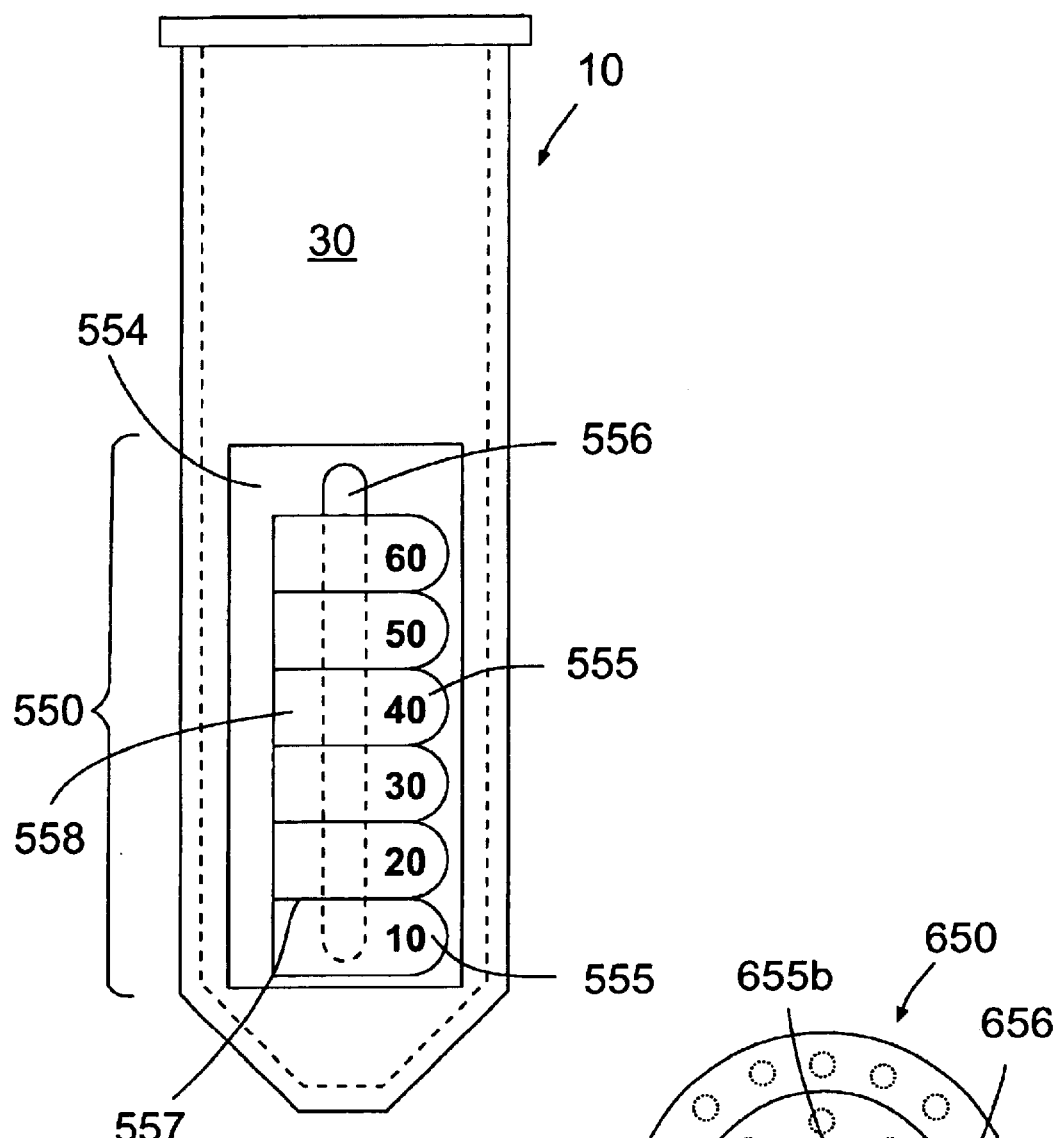
FIG. 5 is a frontal view of a fluid-filtration receptacle 10 according to another embodiment of the present invention, the embodiment being distinguished primarily by the configuration of the receptacle 10's releasably-sealed semi-permeable drain 550.

Referring to FIG. 5, another embodiment of the present invention is shown, with the underdrain support 554 having a through slot 556, so that liquid filtered by membrane (not shown) exits the device through the slot 556. A sealing device 558 covers the slot 556 in a liquid tight manner. The sealing device 558 has one or more tabs 555 and partial cuts 557 so when one of the tabs 555 is pulled the partial cuts 557 fails and only the selected tab 555 is removed, exposing an exit point in the slot 556 that corresponds to the desired concentrate volume.

Figure 6:
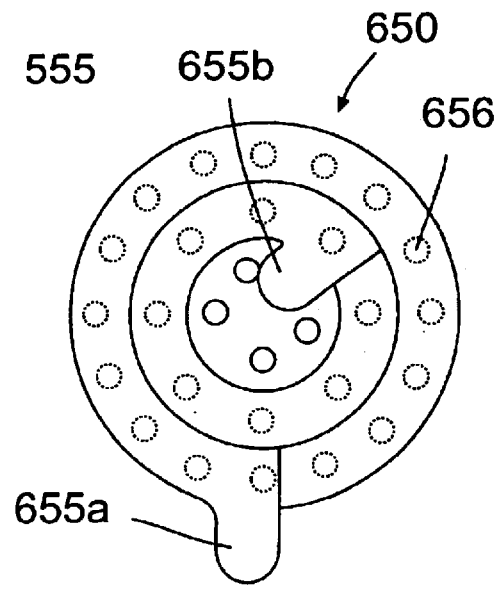
FIG. 6 illustrates a releasably-sealed semi-permeable drain configuration 650 that can be used as an alternative to the drain configuration used in the centrifugal fluid-filtration receptacle 10 illustrated in FIG. 4.

A sealing device 650, suitable for use for example in the fluid-filtration receptacle 210 illustrated in FIG. 2, is shown in FIG. 6. Assuming the fluid-filtration receptacle is round in shape and rotatable within a centrifuge rotor compartment, if the receptacle in FIG. 2 rotates 180 degrees, the sealing device 258 in FIG. 2 would cover drain hole 256a. The fluid-filtration receptacle 210 would not retain the expected volume. Therefore, if the receptacle 210 cannot be easily or otherwise prevented from rotating in a fixed angled rotor, the sealing device 650 shown in FIG. 6, can be used to better control filtration volume. Sealing device 650 comprises one or more concentric rings of film sealed and covering the drain holes 656. If the tab 655b is removed, exposing the middle set of concentric holes, a set volume of sample liquid will be retained in the receptacle, regardless of its orientation within the rotor. The same is true if the tab 655a is removed. The difference being less sample liquid volume will be retained.

Alternatively, the receptacle could be fixed to the rotor, for example, by having a notch formed in the receptacle which locks to a nub in the rotor housing to prevent rotation.

The sealing device of the present invention can be selected from a variety of materials and exist is a variety of forms. All must provide a liquid tight seal when in place, must be capable of being retained in place during use and must be capable of being selectively removed when desired.

Other forms of the sealing components include, but are not limited to, films which may be adhered using adhesives, solvents, heat shrunk or thermally or vibrationally bonded to the housing.

The invention can also implement a series of separate films, each of which cover one level of drain hole(s) to define a set filtration levels in the device. Alternatively, a single film which has been scored or perforated or otherwise segmented into strips each of which cover one level of drain hole(s) can also be used to define a set of specifiable filtration levels. Each can be separately removed as desired.

Another alternative is to use a thin, penetratable film that covers the drain holes. The film can be pierced or otherwise opened as needed.

Alternatively, plugs can be used to seal the drain holes, and can be made from plastic, preferably (but not limited to) an elastomer, and retained by a pressure fit. The plugs may be tapered, may have a bulbous end, and they may have a dovetail-like feature, similar to that of a champagne cork to hold the plugs securely in place until it is desired that they be removed. A handle can be implemented to facilitate removal.

The following are examples of such sealing components.

Figure 7:
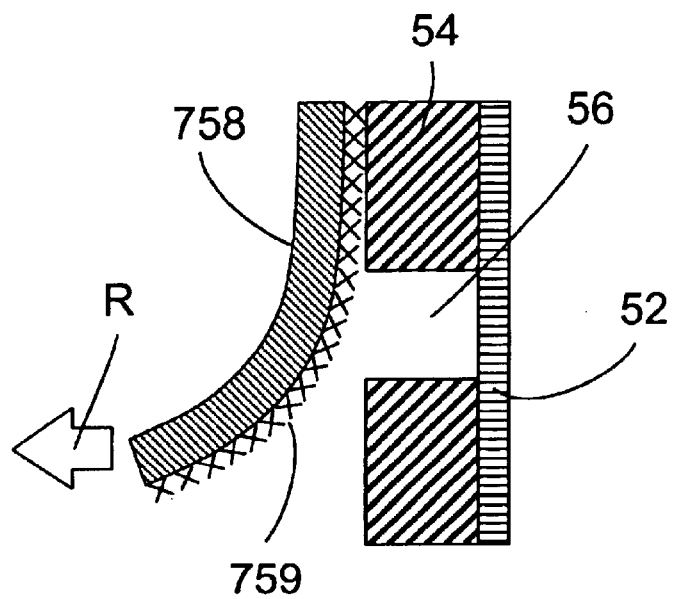
FIG. 7 is a lateral sectional view of a drain hole 56 covered with an adhesively-applied releasable sealing element 758.

Referring to FIG. 7, the drain hole 56 in housing 54 is covered on one side by membrane 52, and on the other side, by a sealing component 758. A pulling force R is applied to one side of the sealing component 758. The adhesive 759 releases and opens drain hole 56 the sealing component 758 can be an adhesive coated onto a plastic film. The adhesive backing being a pressure sensitive, thermally activated, or chemically activated. Regardless, the adhesive should adhere well to the housing and maintain a liquid tight seal during centrifugation, yet be easily removed when selecting the desired filtration volume.

Figure 8:
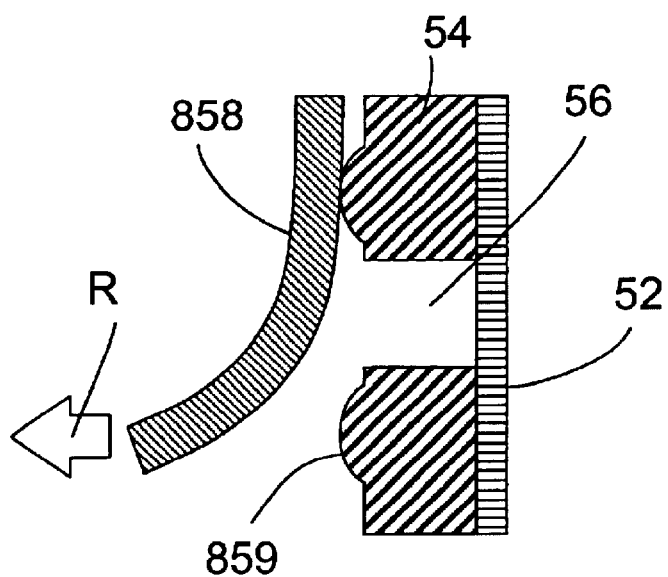
FIG. 8 is a lateral sectional view of a drain hole 56 covered with a thermally-applied releasable sealing element 858.

Referring to FIG. 8, a drain hole 56 in housing 54 is covered on one side by membrane 52, and on the other side, by a heat-sealed sealing component 858. A pulling force R is applied to one side of the heat-sealed sealing component 858. The heat seal at seal ring 859 fails and the sealing device 858 releases opening drain hole 56. The housing and film material are selected in part on the basis of their thermal-bonding capacity. An example of a suitable combination is a polyethylene and polyester laminate applied to a receptacle having a polyethylene housing. The polyester can provide good structural durability for centrifugation and the polyethylene-to-polyethylene bond can provide a liquid-tight thermal seal.

Figure 9:
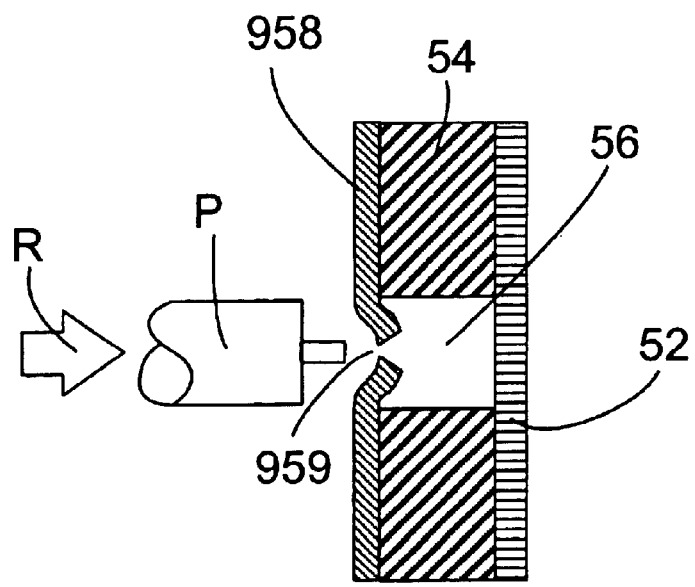
FIG. 9 is a lateral sectional view of a drain hole 56 and a sealing element "released" by the puncturing thereof with a punch P.

Referring to FIG. 9, a drain hole 56 in housing 54 is covered on one side by membrane 52, and on the other side, by a pierceable film sealing component 958. A punch tool P is pushed by a force R sufficient to pierce, penetrate, fracture, or otherwise release the sealing component 958. Punch tool P creates an opening 959 allowing fluid passing through membrane 52 and drain hole 56 to flow through opening 959.

Punch tool P is shown as a "stepped" pin tool. A variety of other punch tool configurations can of course be employed, such as an angled point, a sharp flat blade, or a cross blade design. Regardless, selection and/or use of the tool should be made with an eye towards protecting damage to the membrane when punching through the sealing component. Along these lines, the "step" of punch tool P prevents over-penetration through housing 54, which can damage membrane 52.

Figure 10:
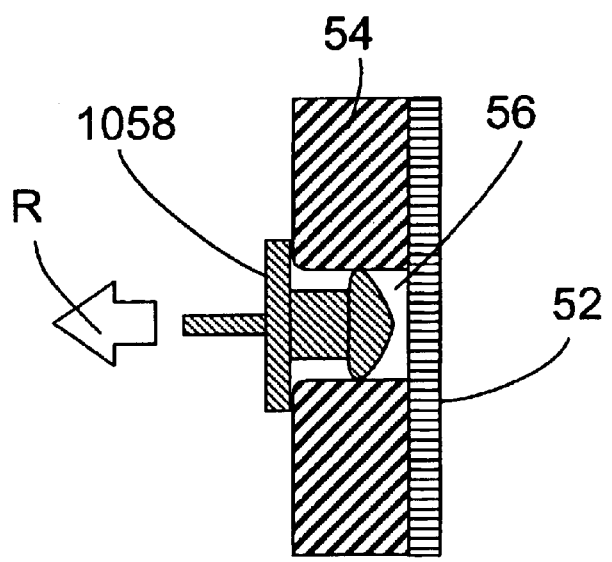
FIG. 10 is a lateral sectional view of a drain hole 56 with a reusable releasable sealing element 1058.

Referring to FIG. 10, a drain hole in housing 54 is covered on one side by membrane 52. At the other end of the drain hole 56, a plug 1058 is used to seal the drain hole 56. To open the drain hole 56 plug 1058 is pulled in the direction R. Examples of suitable materials for plug 1058 are Silicone, Buna-N, Neoprene, Viton and ethylene propylene. The drain holes and plugs can have complimentary tapers similar to luer fittings.

Those skilled in the art, having the benefit of the teaching of the present invention set forth herein, can effect numerous modifications thereto. These modifications are to be construed as being encompassed within the scope of the present invention as set forth in the appended claims.

What is claimed is:

1. A fluid-filtration receptacle capable of containing a liquid when placed in a predetermined range of operative positions, wherein:

(a) the receptacle comprises a user-fillable liquid-containable internal area defined by an at least partially-enclosing liquid-impermeable solid material, the liquid-impermeable solid material having a semi-permeable drain disposed therethrough and a seal component releasably-sealing said semi-permeable drain;

(b) the semi-permeable drain is capable of being either completely or variably unsealed by a user to allow draining of a predetermined corresponding volume of said liquid from said internal area when said receptacle is placed in at least one of said predetermined operative positions; and (c) informative indicia on or proximate said seal component indicative of the predetermined volume of said liquid drained from said internal area when said semi-permeable drain is unsealed.

2. The fluid-filtration receptacle of claim 1, wherein the drain comprises at least one opening and a semi-permeable membrane material, the semi-permeable membrane material being positioned within or superposed over said opening.

3. The fluid-filtration receptacle of claim 2, wherein said seal component is a removable plug.

4. The fluid-filtration receptacle of claim 2, wherein said seal component is a removable thermoplastic covering.

5. The fluid-filtration receptacle of claim 2, wherein said seal component is a removable elastomeric coating.

6. The fluid-filtration receptacle of claim 2, wherein said seal component is a thin user-destructible thermoplastic film, the average thickness of said thermoplastic film being substantially less than the average thickness of said liquid-impermeable solid material.

7. The fluid-filtration receptacle of claim 1, wherein said drain comprises a plurality of discrete, sealed, semi-permeable openings and said seal component comprises a corresponding plurality of independently removable seals, each of said openings capable of being individually and completely unsealed by a user by removal of a corresponding seal.

8. The fluid-filtration receptacle of claim 1, wherein said drain comprises a single, sealed, semi-permeable opening and said seal component comprises a plurality of independently removable seal, said single opening capable of being variably unsealed by a user by removal of one or many of said independently removable seals.

9. A centrifugal filter unit kit comprising the fluid-filtration receptacle of claim 1 and a filtrate collection vial, the fluid-filtration receptacle at least partially fittable within the filtrate collection vial whereby liquid drained from said internal area of said fluid-filtration receptacle collects in said filtrate collection vial.

10. The centrifugal filter unit kit of claim 9, wherein the drain comprises at least one opening and a semi-permeable membrane material, the semi-permeable membrane material being positioned within or superposed over said opening.

11. A fluid-filtration receptacle capable of containing a liquid when placed in a predetermined range of operative positions, wherein:

(a) the receptacle comprises a user-fillable liquid-containable internal area defined by an at least partially-enclosing liquid-impermeable solid material, the liquid-impermeable solid material having a semi-permeable drain disposed therethrough and a seal component releasably-sealing said semi-permeable drain; and (b) the semi-permeable drain comprises a plurality of discrete semi-permeable openings and the seal component comprises a corresponding plurality of independently removable seals, each of said openings capable of being individually and completely unsealed by a user by removal of one of said corresponding plurality of independently removable seals, whereby the semipermeable drain is capable of being variably unsealed to allow draining of corresponding predetermined volumes of said liquid from said internal area when said receptacle is placed in at least one of said predetermined operative positions.

12. A centrifugal filter unit kit comprising the fluid-filtration receptacle of claim 11 and a filtrate collection vial, the fluid-filtration receptacle at least partially fittable within the filtrate collection vial whereby liquid drained from said internal area of said fluid-filtration receptacle collects in said filtrate collection vial.

* * * * *